(12) United States Patent
Castillo et al.

(10) Patent No.: US 8,882,689 B2
(45) Date of Patent: Nov. 11, 2014

(54) KNEE BRACE

(75) Inventors: David Castillo, Lake Forest, CA (US); Daniel Castillo, Laguna Beach, CA (US)

(73) Assignee: Asterisk.Asterisk, LLC, Lake Forest, CA (US)

( * ) Notice: Subject to any disclaimer, the term of this patent is extended or adjusted under 35 U.S.C. 154(b) by 322 days.

(21) Appl. No.: 12/973,645

(22) Filed: Dec. 20, 2010

(65) Prior Publication Data
US 2012/0157902 A1 Jun. 21, 2012

(51) Int. Cl.
*A61F 5/00* (2006.01)

(52) U.S. Cl.
USPC .............................................. 602/23; 602/26

(58) Field of Classification Search
USPC .................... 602/5, 16, 23–27, 5.16; 128/882
See application file for complete search history.

(56) References Cited

U.S. PATENT DOCUMENTS

| | | |
|---|---|---|
| 1,081,148 A | 12/1913 | Quayle |
| 1,388,772 A | 8/1921 | Sheehan |
| 1,390,915 A | 9/1921 | Alwin |
| 2,531,486 A | 11/1950 | Weber |
| 2,557,604 A | 6/1951 | Invidiato |
| 2,558,986 A | 7/1951 | Seelert |
| 2,812,961 A | 11/1957 | Brown et al. |
| 2,883,982 A | 4/1959 | Rainey |
| 3,030,634 A | 4/1962 | Bair |
| 3,045,243 A | 7/1962 | Seymour |
| 3,099,448 A | 7/1963 | Salvo et al. |
| 3,387,305 A | 6/1968 | Shafer |
| 3,669,105 A | 6/1972 | Castiglia |
| 3,779,654 A | 12/1973 | Horne |
| 3,785,372 A | 1/1974 | Craig |
| 3,817,244 A | 6/1974 | Taylor |
| 3,900,898 A | 8/1975 | Ackerman et al. |
| 3,901,223 A | 8/1975 | May et al. |
| 3,902,482 A | 9/1975 | Taylor et al. |
| 3,928,872 A | 12/1975 | Johnson et al. |
| 3,958,569 A | 5/1976 | Vosburgh |
| 4,136,404 A | 1/1979 | Lange |

(Continued)

FOREIGN PATENT DOCUMENTS

| | | |
|---|---|---|
| DE | 1491569 A1 | 7/1969 |
| DE | 2432766 A1 | 3/1975 |
| EP | 297766 A1 | 1/1989 |
| WO | 8404240 A1 | 11/1984 |

OTHER PUBLICATIONS

Alpinestars; Carbon B2 Knee Brace; 1 page.

*Primary Examiner* — Michael A. Brown
(74) *Attorney, Agent, or Firm* — Stetina Brunda Garred & Brucker (57) ABSTRACT

Provided is a brace including upper and lower frame members and upper and lower cuff members. An upper adjuster is coupled to the upper frame member and upper cuff member and is configured to enable selective adjustment of the distance between the upper frame member and the upper cuff member. An upper connector is coupled to the upper frame member and the upper cuff member and is configured to enable selective engagement between the upper frame member and the upper cuff member. A lower adjuster is coupled to the lower frame member and the lower cuff member and is configured to enable selective adjustment of the distance between the lower frame member and the lower cuff member. A lower connector is coupled to the lower frame member and the lower cuff member and is configured to enable selective engagement between the lower frame member and the lower cuff member.

2 Claims, 5 Drawing Sheets

(56) References Cited

U.S. PATENT DOCUMENTS

| | | |
|---|---|---|
| 4,169,467 A | 10/1979 | Rabischong |
| 4,241,730 A | 12/1980 | Helfet |
| 4,271,831 A | 6/1981 | Deibert |
| 4,361,142 A | 11/1982 | Lewis et al. |
| 4,372,298 A | 2/1983 | Lerman |
| 4,381,768 A | 5/1983 | Erichsen et al. |
| D269,379 S | 6/1983 | Bledsoe |
| 4,407,276 A | 10/1983 | Bledsoe |
| 4,428,369 A | 1/1984 | Peckham et al. |
| 4,450,832 A | 5/1984 | Waddell |
| 4,487,200 A | 12/1984 | Feanny |
| 4,489,718 A | 12/1984 | Martin |
| 4,493,316 A | 1/1985 | Reed et al. |
| 4,523,585 A | 6/1985 | Lamb et al. |
| 4,554,913 A | 11/1985 | Womack et al. |
| D284,702 S | 7/1986 | Castillo |
| 4,800,629 A | 1/1989 | Ikeda |
| 4,805,606 A | 2/1989 | McDavid |
| 5,222,279 A | 6/1993 | Frano |
| 5,599,288 A | 2/1997 | Shirley |
| 6,289,558 B1 | 9/2001 | Hammerslag |
| 6,461,318 B2 | 10/2002 | Freeman et al. |
| 6,464,657 B1 | 10/2002 | Castillo |
| 6,689,080 B2 | 2/2004 | Castillo |
| 6,746,248 B2 | 6/2004 | Eastwood |
| 6,793,641 B2 | 9/2004 | Freeman et al. |
| 6,796,951 B2 | 9/2004 | Freeman et al. |
| 6,962,571 B2 | 11/2005 | Castillo |
| 7,117,569 B2 | 10/2006 | Bledsoe |
| 7,122,016 B1 | 10/2006 | DeToro |
| 7,182,740 B1 | 2/2007 | Castillo |
| D548,844 S | 8/2007 | Castillo |
| 7,458,949 B2 | 12/2008 | Castillo et al. |
| 7,578,800 B2 | 8/2009 | Castillo et al. |
| 7,591,050 B2 | 9/2009 | Hammerslag |
| 7,686,776 B2 | 3/2010 | Castillo et al. |
| 8,277,401 B2 * | 10/2012 | Hammerslag et al. ............ 602/5 |
| 2002/0107464 A1 * | 8/2002 | Castillo ......................... 602/16 |
| 2006/0135900 A1 * | 6/2006 | Ingimundarson et al. ...... 602/26 |
| 2007/0126211 A1 | 6/2007 | Moerke |

\* cited by examiner

KNEE BRACE

CROSS-REFERENCE TO RELATED APPLICATIONS

Not Applicable

STATEMENT RE: FEDERALLY SPONSORED RESEARCH/DEVELOPMENT

Not Applicable

BACKGROUND

1. Field of Invention

This invention relates in general to braces for joint support. Specifically, the invention relates to an exteriorly positionable anatomical brace including a connector for connecting the brace to the user, as well as a separate adjuster for adjusting (i.e., tighten or loosen) the brace on the user.

2. Description

The human body is comprised of a many different joints. Both injury and disease can affect the health, well-being, and operability of the various joints of the human body. Chief among such joints are the knee and elbow, where disease such as osteo-arthritis can curtail normal activity or where an injury such as a sports-related abuse or impact can prevent or severely limit continued activity. Many joint injuries occur when the ligaments holding the joint together tear, either completely or partially.

The knee joint is one of the body's most delicate joints making it prone to injury. The femur, tibia, and fibula are the bones within the leg that comprise the knee joint. The bones are connected by four ligaments. Two collateral ligaments are located on the outside of the knee and control the lateral motion of the knee. The anterior cruciate ligament (ACL) and posterior cruciate ligament (PCL) control rotation of the knee as well as the forward and backward motion of the knee. An injury to any joint, including the knee, is likely to occur when an excessive force is applied to the joint, which may cause the bones to displace beyond its allowable limits, thereby tearing the ligaments.

One method of preventing or reducing the risk of joint injuries is to fit the joint with a brace. The brace provides added stability and support to the particular joint by mitigating damaging movement of the joint (i.e., over-extension).

Braces are configured for use on individuals that vary in size. For instance, a knee brace may be adaptable for use on a user having a leg defining a large circumference or a small circumference. In order to accommodate the various sized limbs which the brace may be disposed on, conventional braces typically include an adjustment mechanism that is adjusted prior to the brace being placed on the limb. In other words, in order for the brace to be properly fitted to the user, the user must adjust the brace to the particular size of the user before the user places the brace on his limb. Ensuring that the brace is properly sized is generally critical to the effectiveness of the brace, i.e., if the brace is not sized correctly, the brace may be ineffective. Accordingly, the process of adjusting and sizing the brace is typically performed on a routine basis, and in some instances, the brace is resized each time the brace is placed on the user's limb.

Although the adaptability of the brace is advantageous in many respects, the process of adjusting the brace may be very time consuming and frustrating. Furthermore, many braces are configured such that adjustment can only take place when the brace is disconnected from the limb. Therefore, once the user has placed the brace on his limb and the user would like to tighten or loosen the brace, it may be necessary to completely disconnect the brace to make such an adjustment.

As such, there is a need in the art for a joint brace that is configured to provide easy adjustment of the brace to allow the user to place the brace on the user's limb without requiring adjustment each time the brace is placed on the limb. The present invention address this particular need, as will be discussed in more detail below.

BRIEF SUMMARY

According to an aspect of the present invention, there is provided a knee brace including an upper frame member having a first upper side section and a second upper side section. A lower frame member is pivotally coupled to the upper frame member and includes a first lower side section and a second lower side section. The brace further includes an upper cuff member having a first upper side section and a second upper side section, and a lower cuff member having a first lower side section and a second lower side section. An upper adjuster is coupled to the first upper side section of upper frame member and the first upper side section of the upper cuff member. The upper adjuster is configured to enable selective adjustment of the distance between the first upper side section of the upper frame member and the first upper side section of the upper cuff member. An upper connector is coupled to the second upper side section of the upper frame member and the second upper side section of the upper cuff member. The upper connector is configured to enable selective engagement between the second upper side section of the upper frame member and the second upper side section of the upper cuff member. A lower adjuster is coupled to the first lower side section of lower frame member and the first lower side section of the lower cuff member. The lower adjuster is configured to enable selective adjustment of the distance between the first lower side section of the lower frame member and the first lower side section of the lower cuff member. A lower connector is coupled to the second lower side section of the lower frame member and the second lower side section of the lower cuff member. The lower connector is configured to enable selective engagement between the second lower side section of the lower frame member and the second lower side section of the lower cuff member.

According to another embodiment, there is provided a knee brace including a first assembly defining a first adjustment section and a first connecting section, with the first assembly including a first frame member and a first cuff member. A first adjuster is coupled to the first frame member and the first cuff member. The first adjuster is configured to enable selective adjustment of the distance between the first frame member and the first cuff member adjacent the first adjustment section. A first connector is coupled to the first frame member and the first cuff member. The first connector is configured to enable selective engagement between the first frame member and the first cuff member adjacent the first connecting section. The brace further includes a second assembly pivotally coupled to the first assembly.

The present invention is best understood by reference to the following detailed description when read in conjunction with the accompanying drawings.

BRIEF DESCRIPTION OF THE DRAWINGS

These and other features and advantages of the various embodiments disclosed herein will be better understood with respect to the following description and drawings, in which like numbers refer to like parts throughout, and in which.

DETAILED DESCRIPTION

The detailed description set forth below is intended as a description of the presently preferred embodiment of the invention, and is not intended to represent the only form in which the present invention may be constructed or utilized. The description sets forth the functions and sequences of steps for constructing and operating the invention. It is to be understood, however, that the same or equivalent functions and sequences may be accomplished by different embodiments and that they are also intended to be encompassed within the scope of the invention.

Referring now to the drawings, wherein the showings are for purposes of illustrating preferred embodiments of the present invention only, and not for purposes of limiting the same, there is depicted a knee brace 10 configured to simplify adjustment and attachment of the knee brace 10 to the user 12. More specifically, the knee brace 10 includes one or more adjusters configured to allow for quick and easy gross adjustment of the knee brace 10 to adjust the size of the knee brace 10 to conform to the user 12. The adjustment of the knee brace 10 is preferably performed prior to the initial securement of the knee brace 10 upon the user 12. The knee brace 10 additionally includes one or more connectors to attach or secure the knee brace 10 to the user 12 and to tighten the knee brace 10 to the user's limb. To remove the knee brace 10, the user 12 disengages the connectors and removes the knee brace 10 from the user 12. The adjusters do not require disengagement to remove the knee brace 10 from the user 12. Rather, the adjusters maintain the knee brace 10 in the customized size set by the user 12. Therefore, when the user 12 subsequently uses the knee brace 10, the knee brace 10 is already in the customized size for the user 12.

Referring now specifically to FIGS. 1-4, the knee brace 10 includes an upper frame member 14 and a lower frame member 16 pivotably connected to the upper frame member 14. The upper frame member 14 includes a first upper side section 18 and a second upper section 20 (See FIG. 1). The lower frame member 16 includes a first lower side section 22 and a second lower side section 24 (See FIG. 1). The knee brace 10 further includes an upper cuff member 26 and a lower cuff member 28 (See FIGS. 3 and 4). The upper cuff member 26 includes a first upper side section 30 and a second upper side section 32, and the lower cuff member 28 includes a first lower side section 34 and a second lower side section 36. In general, the frame members 14, 16 are positionable on the front side of the knee, while the cuff members 26, 28 wrap around the back side of the knee.

Figures 1, 2:
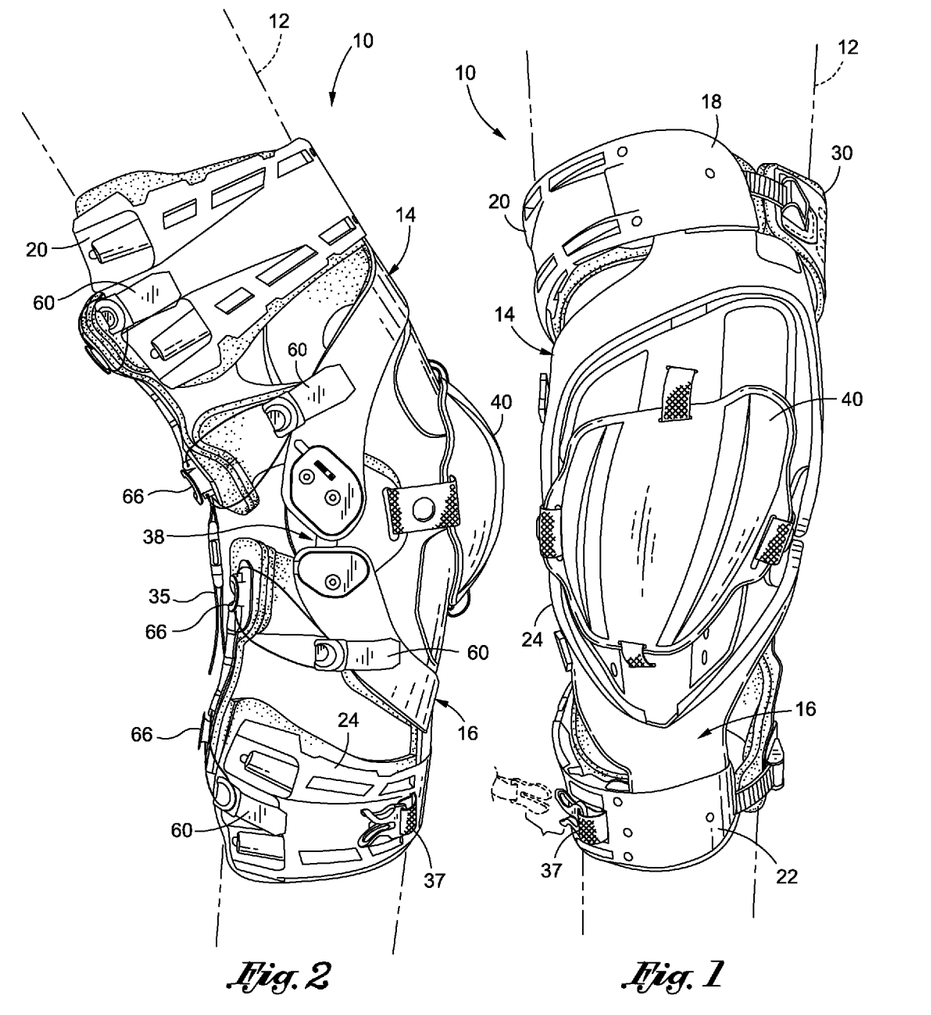
FIG. 1 is front view of a knee brace having a plurality of connectors and a plurality of adjusters.
FIG. 2 is a side view of the knee brace depicted in FIG. 1.
Figures 3, 4:
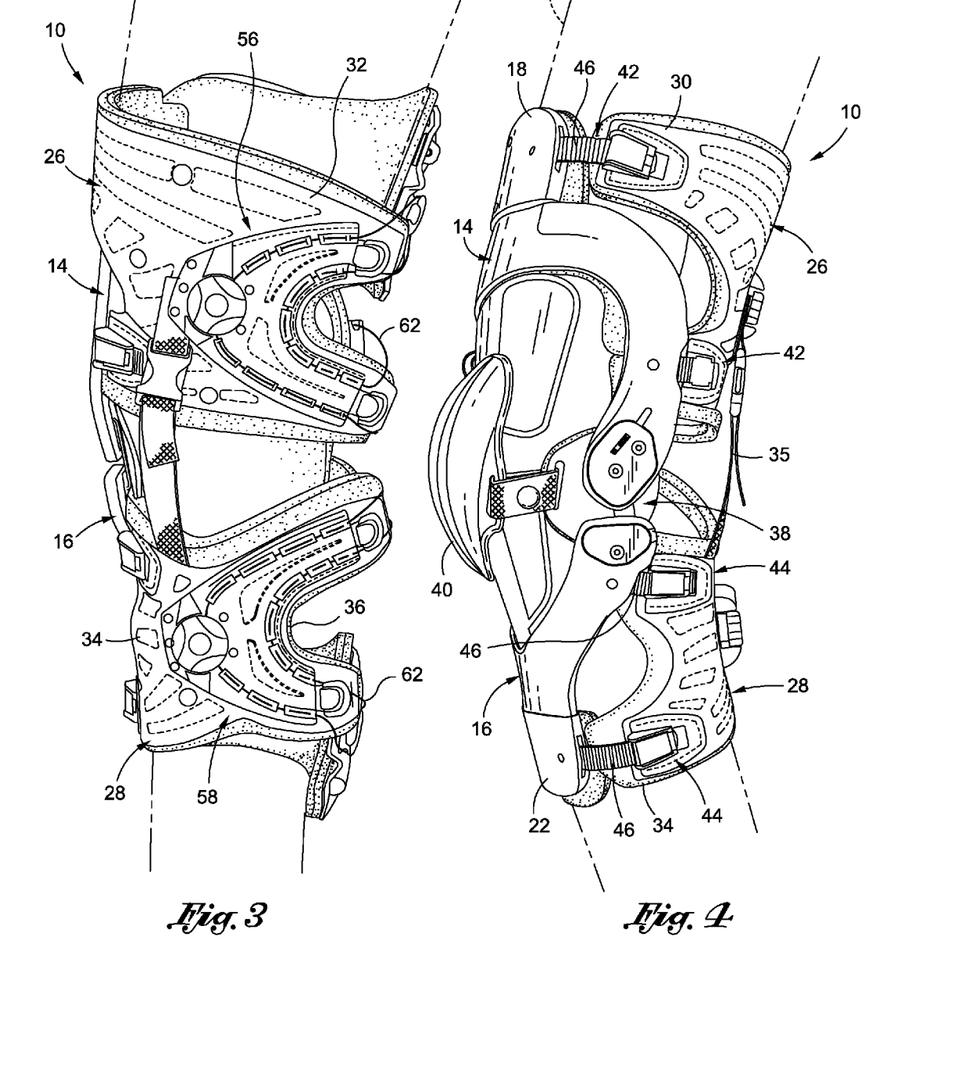
FIG. 3 is a rear view of the knee brace depicted in FIG. 1.
FIG. 4 is a side view of the brace showing the opposing side of the brace shown in FIG. 2.

The upper frame member 14 and the lower frame member 16 are connected by a pair of opposed pivot members 38 (See FIGS. 2 and 4). The pivot members 38 are configured to simulate the natural pivoting motion of the respective joint (i.e., the joint associated with brace 10, such as the knee joint or elbow joint). The pivot members 38 may also be configured to limit the pivotal range of motion of the knee brace 10. For a more detailed description of the pivot members 38, please refer to co-owned U.S. Pat. No. 6,962,571, entitled Joint Brace with Multi-planar Pivoting Assembly and Infinitely Adjustable Limb Extension Regulator, the entire contents of which are expressly incorporated herein by reference.

Referring now specifically to FIG. 4, it is additionally contemplated that the brace 10 includes a strap 35 extending between the upper cuff member 26 and the lower cuff member 28 for restricting the range of motion of the upper portion of the brace 10 relative to the lower portion of the brace 10. The strap 35 may serve as a redundant limiting member (i.e., in addition to the pivot member 38), or as a stand-alone limiting member (i.e., in embodiments where the pivot member 38 does not limit the pivotal range of motion of the frame members 14, 16).

The brace 10 may also include a boot connector strap 37 (See FIGS. 1 and 2) for connecting the brace 10 to a boot or other footwear article (not shown). The boot connector strap 37 may be configured to limit the rotational range of motion of the brace 10 relative to the boot to mitigate injury to the knee joint. For a more in-depth discussion of the boot connector strap 37 and connecting the knee brace 10 to a boot, please refer to co-owned U.S. Pat. No. 7,578,800, entitled Flexible Tether Member Connecting a Knee Brace to a Boot, the entire contents of which are incorporated herein by reference.

The knee brace 10 may additionally include a knee cap cover 40 for protecting the knee cap of the user 12. The knee cap cover 40 may be formed from a lightweight, durable material, such as plastic, rubber, or other materials known by those skilled in the art. The knee cap cover 40 is connected to the upper frame member 14, lower frame member 16, and pivot members 38 by a plurality of straps, which may be unfastened to remove the knee cap cover 40 from the knee brace 10.

The upper frame member 14 and upper cuff member 26 define a first assembly which collectively circumscribe a first limb structure (i.e., the user's thigh), while the lower frame member 16 and lower cuff member 28 define a second assembly which collectively circumscribe a second limb structure (i.e., the user's shin and calf). The circumferential size collectively defined by the upper frame member 14 and upper cuff member 26 may be adjusted to conform to the circumferential size of the first limb structure. Likewise, the circumferential size collectively defined by the lower frame member 16 and lower cuff member 28 may be adjusted to the circumferential size of the user's second limb member. The circumferential size is adjusted by moving the respective cuff members 26, 28 relative to the respective frame members 14, 16.

The position of the respective cuff members 26, 28 relative to the respective frame members 14, 16 is controlled by an adjuster. Referring now specifically to FIG. 4, the knee brace 10 depicted therein includes four adjusters, namely, a pair of upper adjusters 42 for controlling the position of the upper cuff member 26 relative to the upper frame member 14, and a pair of lower adjusters 44 for controlling the position of the lower cuff member 28 relative to the lower frame member 16. The upper adjusters 42 are connected to the upper frame member 14 and the upper cuff member 26 and are configured to enable selective adjustment of the distance between the upper frame member 14 and the upper cuff member 26 adjacent a first adjustment section. More specifically, the upper adjusters 42 are connected to the first upper side section 18 of the upper frame member 14 and the first upper side section 30 of the upper cuff member 26. The upper adjusters 42 are configured to enable selective adjustment of the distance between the first upper side section 18 of the upper frame member 14 and the first upper side section 30 of the upper cuff member 26. Similarly, the lower adjusters 44 are coupled to the lower frame member 16 and the lower cuff member 28 and are configured to enable selective adjustment of the distance between the lower frame member 16 and the lower cuff member 28 adjacent a second adjustment section. More specifically, the lower adjusters 44 are coupled to the first lower side section 22 of the lower frame member 16 and the first lower side section 34 of the lower cuff member 28. The lower adjusters 44 are configured to enable selective adjustment of the distance between the first lower side section 22 of the lower frame member 16 and the first lower side section 34 of the lower cuff member 28.

Figure 5:
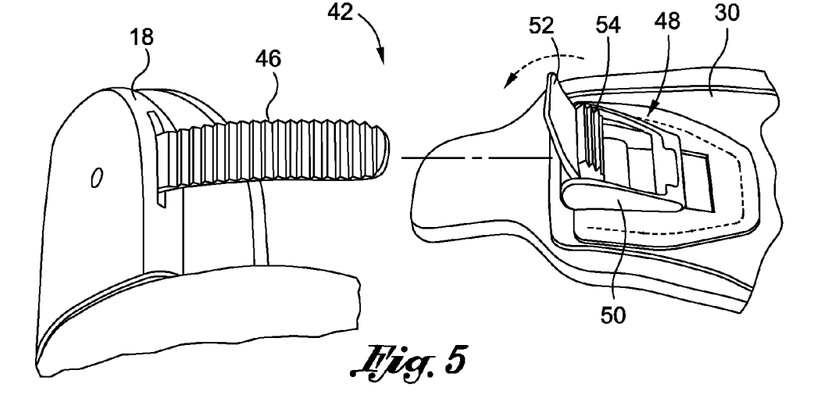
FIG. 5 is an upper perspective view of an adjuster having a toothed band and a locking mechanism, the toothed band being disengaged from the locking mechanism.
Figure 6:
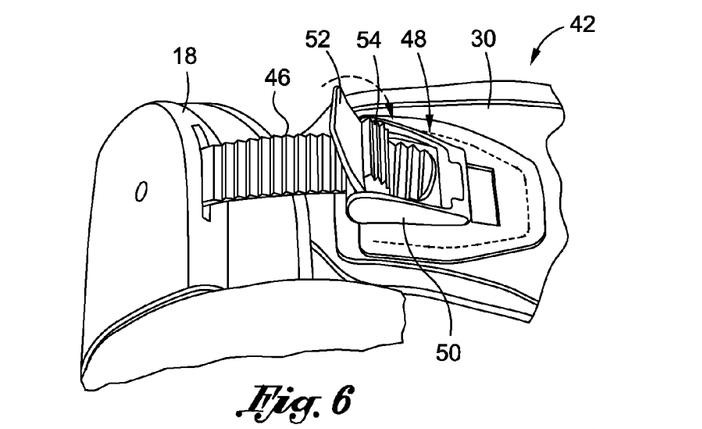
FIG. 6 is an upper perspective view of the adjuster with the toothed band advanced into the locking mechanism, with the locking mechanism being in an unlocked configuration to allow for movement of the toothed band relative to the locking mechanism.
Figure 7:
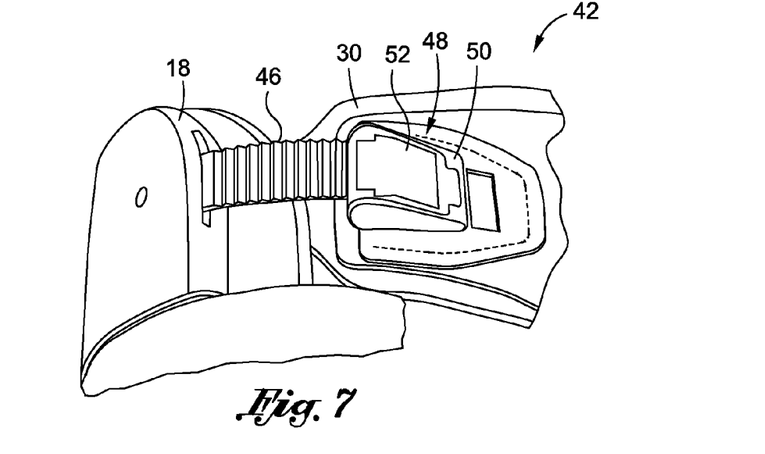
FIG. 7 is an upper perspective view of the adjuster with the locking member being disposed in a locked configuration to mitigate removal of the toothed band.

Referring now specifically to FIGS. 5-7, there is shown an upper adjuster 42 progressing from a disengaged configuration to an adjusting configuration, and finally to a locked configuration. Although FIGS. 5-7 depict an upper adjuster 42, those skilled in the art will appreciate that the discussion pertaining to FIGS. 5-7 may apply equally to a lower adjuster 44. The adjuster 42 includes a tooth band 46 coupled to the upper frame member 14 and a complimentary locking mechanism 48 coupled to the upper cuff member 26. The locking mechanism 48 includes a base 50 and a pivoting arm 52 having a tooth locking portion 54. The pivoting arm 52 is pivotable relative to the base 50 between an unlocked configuration, as shown in FIGS. 5 and 6, and a locked configuration, as shown in FIG. 7. When the pivoting arm 52 is in the unlocked configuration, the tooth band 46 may slide between the pivoting arm 52 and the base 50. As the band 46 slides relative to the locking mechanism 48, the circumferential size defined by the upper frame member 14 and the upper cuff member 26 is adjusted. More specifically, as the band 46 is advanced further into the locking mechanism 48, the circumferential size decreases, and conversely, as the band 46 is withdrawn from the locking mechanism 48, the circumferential size increases. The band 46 may be positioned relative to the locking mechanism 48 to achieve the desired circumferential fit to conform to the size of the user 12.

When the upper frame member 14 and upper cuff member 16 have been positioned to achieve the desired circumferential size, the pivoting arm 52 is pivoted toward the locked configuration to restrict further movement of the band 46 relative to the locking mechanism 48. In the locked position, the toothed locking portion 54 engages with the toothed band 46 to mitigate movement of the tooth banded 46 relative to the locking mechanism 48. In this regard, the circumferential size is roughly fixed until further adjustment by the user 12. As will be described in more detail below, smaller or finer adjustment of the circumferential size may be achieved via connectors used to fasten the knee brace 10 to the user 12. However, the rough or gross circumferential size remains fixed and does not require readjustment for each use.

Referring now back to FIG. 4, the knee brace 10 includes to upper adjusters 42 extending between the upper frame member 14 and the upper cuff member 26, and two lower adjusters 44 extending between the lower frame member 16 and the lower cuff member 28. It is preferred that the upper adjusters 42 and lower adjusters 44 are disposed on a common side of the knee brace 10, such as the medial side or the lateral side. In this regard, the side including the adjusters 42, 44 remains closed, while an opposing side may be opened to place the knee brace 10 on the user 12. This is best depicted in FIGS. 1 and 4, which show opposed sides of the knee brace 10, with one side including connectors for securing the knee brace 10 to the user 12 (see FIG. 1), and the other side including the adjusters 42, 44 for adjusting the circumferential size of the knee brace 10 (see FIG. 4). A plurality of upper adjusters 42 and lower adjusters 44 may provide distinct circumferential adjustment zones. In this regard, each circumferential adjustment zone may be individually adjusted to provide a greater degree of conformity to the user's limb.

The knee brace 10 further includes a plurality of connectors for securing/attaching the brace 10 to the user's limb. More specifically, the knee brace 10 includes an upper connector 56 for securing the upper frame member 14 and upper cuff member 26 to the user 12, and a lower connector 58 for connecting the lower frame member 16 and the lower cuff member 28 to the user 12. The connectors 56, 58 are moveable between a disconnected configuration, wherein the frame member and cuff member may be separated to place the knee brace 10 on the user 12, and a connected configuration, to fasten the knee brace 10 upon the user 12. The connectors 56, 58 are also adjustable in the connected configuration to tighten or loosen the knee brace 10 upon the user 12.

The upper connector 56 is coupled to the upper frame member 14 and the upper cuff member 26 and is configured to enable selective engagement between the upper frame member 14 and the upper cuff member 26 adjacent a first connecting section. More specifically, the upper connector 56 is connected to the second upper side section of the upper frame member 14 and the second upper side section 32 of the upper cuff member 26. The lower connector 58 is coupled to the lower frame member 16 and the lower cuff member 28 and is configured to enable selective engagement between the lower frame member 16 and the lower cuff member 28 adjacent a second adjustment section. More specifically, the lower connector 58 is coupled to the second lower side section 24 of the lower frame member 16 and the second lower side section 36 of the lower cuff member 28.

Figure 8:
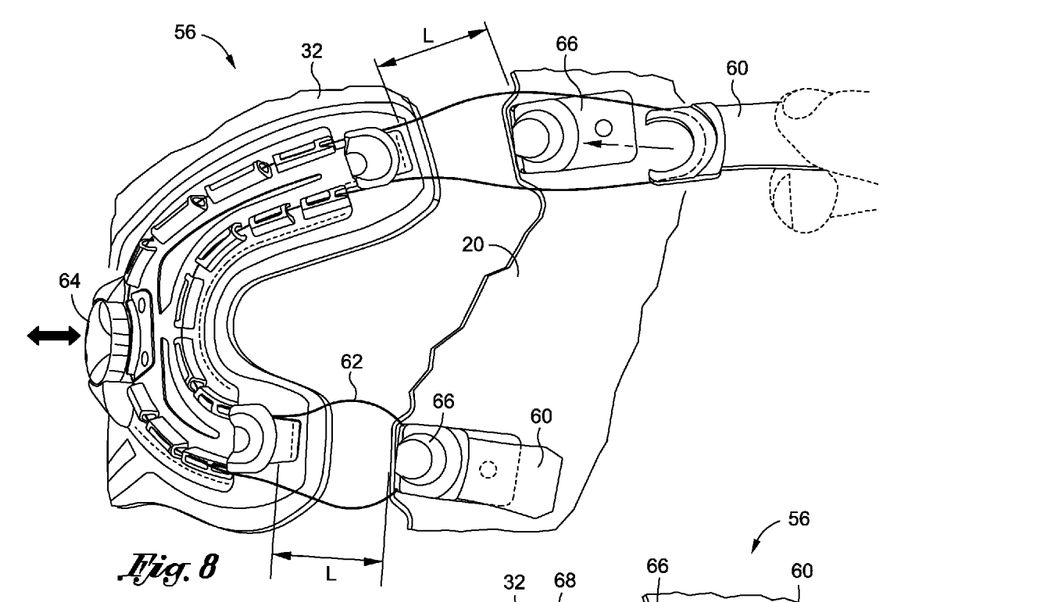
FIG. 8 is an upper perspective view of a connector including a pair of primary connectors, a pair of secondary connectors, a tether coupled to the pair of primary connectors, and an adjustment dial for controlling the length of the tether.
Figure 9:
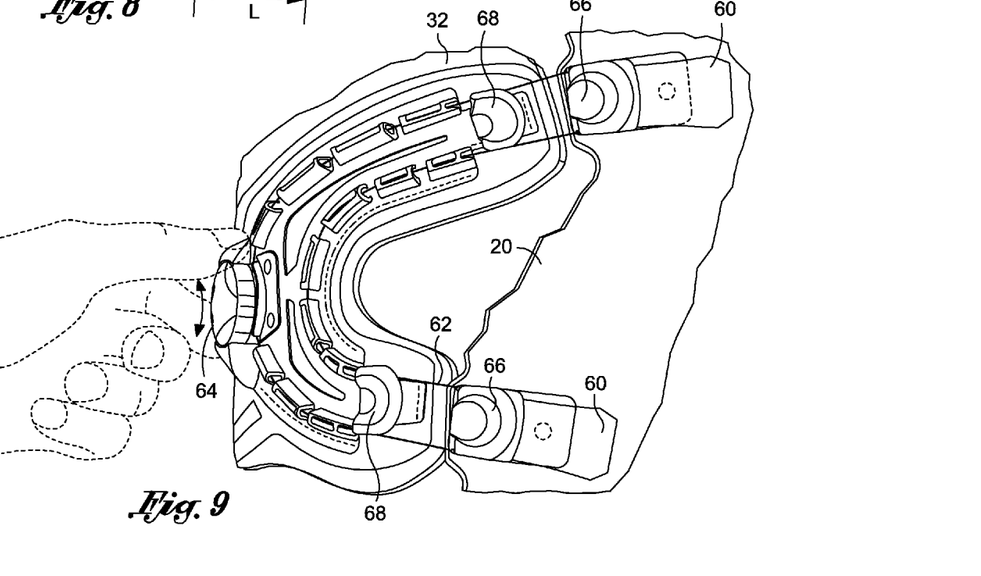
FIG. 9 is an upper perspective view of the connector with the pair of primary connectors being engaged with respective ones of the pair of secondary connectors.
Figure 10:
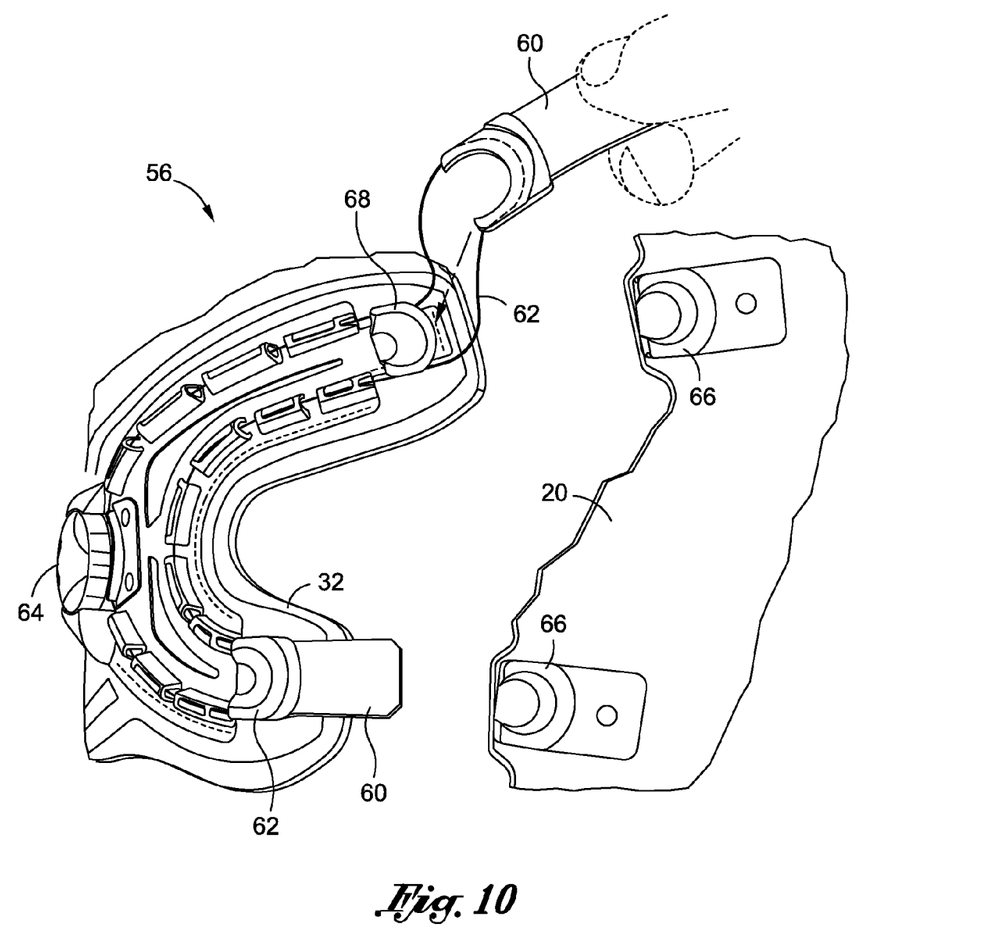
FIG. 10 is an upper perspective view of the connector with the primary connectors being engageable with a pair of respective stow members.

Referring now to FIGS. 8-10, the upper connector 56 is shown in a partially connected configuration (see FIG. 8), a completely connected configuration (see FIG. 9), and a partially stowed configuration (see FIG. 10). Although FIGS. 8-10, and the corresponding description pertain to an upper connector 56, those skilled in the art will appreciate that the drawings and related discussion may apply equally to the lower connector 58.

The upper connector 56 includes a pair of primary connectors 60 coupled to a tether 62 (e.g., cord), which is in turn, coupled to a retraction mechanism 64 (e.g., mechanical tensioner) mounted to the upper cuff member 26. Each primary connector 62 is cooperatively engageable with respective ones of a pair of secondary connectors 66 mounted on the upper frame member 14. The primary connectors 62 engage with the secondary connectors 66 as the tether 62 is retracted by the retraction mechanism 64. When the primary connectors 62 are engaged with respective ones of the secondary connector 66 and the tension in the tether 62 increases, the circumferential size defined by the upper frame member 14 and upper cuff member 26 decreases to conform to the size of the user's limb.

The tension in the tether 62 may be controlled by the retraction mechanism 64, which is selectively disposable in a locked configuration and an unlocked configuration. In the locked configuration, the retraction mechanism 64 is configured to mitigate extension of the tether 62. In the unlocked configuration, the retraction mechanism 64 is configured to allow for extension of the tether 62. The retraction mechanism 64 may be selectively moveable between the locked configuration and unlocked configuration to control the tension in the tether 62.

In the embodiment depicted in FIGS. 8-10, the retraction mechanism 64 includes a dial that is moveable in an axial direction between the locked configuration and the unlocked configuration. The dial is also rotatable to retract the tether 62 and to increase the tension within the tether 62.

The upper connector 56 may also include a stowage connector 68 cooperatively engageable with the primary connector when the brace 10 is not being used. In this regard, the primary connector 60 may be disengaged with the secondary connector 66 and engaged with the stowage connector 68 between uses of the brace 10. When the primary connector 60 is engaged with the stowage connector 68, the retraction mechanism 64 may be used to retract the tether 62 to remove any "slack" in the tether 62.

The exemplary connectors 56, 58 shown in the figures embody the lacing system and lace lock technology manufactured by Boa Technology, Inc. For a more detailed discussion pertaining to the lacing system and lace lock technology, please refer to U.S. Pat. Nos. 6,289,558 and 7,591,050, both entitled Footwear Lacing System, the contents of which are expressly incorporated herein by reference. Those skilled in the art will appreciate that the Boa lacing system is exemplary in nature only and that other connectors may be used without departing from the spirit and scope of the present invention.

With the structure of the brace 10 being described above, the following discussion will focus on usage of the brace 10. Upon initial usage of the brace 10 by a user, the user grossly adjusts the brace 10 to conform to the size of the user's limb. More specifically, the user disposes the brace 10 about the user's limb 12 and uses the upper adjuster 42 to adjust the circumferential size defined by the upper frame member 14 and the upper cuff member 26 and the lower adjuster 44 to adjust the circumferential size defined by the lower frame member 16 and the lower cuff member 28.

With the gross adjustment of the brace 10 being complete, the user may then connect the brace 10 to the user's limb 12 by employing the upper connector 56 and the lower connector 58. Prior to use, the primary connectors 60 may be engaged with respective stowage connectors 68. To connect the brace 10 to the user's limb 12, the primary connectors 60 are disengaged from the stowage connectors 68 and moved into engagement with the secondary connectors 66. In order to move the primary connectors 60 from the stowage connector 68 to the secondary connector 66, the tether 62 is extended by moving the retraction mechanism 64 to the unlocked configuration to allow the tether 62 to be extended. After there is enough slack in the tether 62 to place the primary connector 60 into engagement with a respective one of the secondary connectors 66, the tether 62 may be retracted. Along these lines, the retraction mechanism 64 is moved into the locked configuration and is rotated to retract the tether 62. As the tension increases in the tether, the circumferential size defined by the respective frame member and cuff member decreases to customize the fit of the brace 10 to the particular user. More specifically, the distance "L" (see FIG. 8) disposed between the secondary connector 66 and stowage connector 68 decreases as the tension in the tether 62 increases.

With the brace 10 properly fitted to the user 12, the user 12 may maximize the comfort and protection afforded by the brace 10. If the user 12 desires to make minor adjustments to the brace 10, the connectors 56, 58 may be used to make such adjustments (i.e., by increasing or decreasing the length of the tether 62).

To remove the brace 10, the user 12 simply disconnects the upper connector 56 and lower connector 58 by moving the respective retraction mechanism 64 into the unlocked configuration to allow for extension of the tether 62 for disengaging the primary connector 60 from the secondary connector 66. The retraction mechanism 64 is then returned to the locked configuration to retract the tether 62 to engage the primary connectors 60 with the stowage connectors 68.

When the user 12 desires to use the brace 10 during a subsequent usage, the user may not be required to make adjustments to the upper and lower adjusters 42. Rather, the brace 10 continues to define the size made prior to the initial usage of the brace 10 (i.e., the gross adjustments made via the upper adjuster 42 and lower adjuster 44). Therefore, subsequent uses of the brace 10 simply require attachment to the user via the upper and lower connectors 56, 58, as described in more detail above.

The above description is given by way of example, and not limitation. Given the above disclosure, one skilled in the art could devise variations that are within the scope and spirit of the invention disclosed herein. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. A knee brace comprising:

upper and lower rigid frame members pivotally coupled to each other;

an upper cuff separate from the upper rigid frame member and having opposed first and second upper side sections, the upper cuff being selectively connectable to the upper frame member via separate connections adjacent the first and second upper side sections;

a gross adjustment upper connector configured to connect the upper cuff to the upper frame member at one of the first and second upper side sections such that the upper cuff and upper rigid frame member define an arcuate dimension, the upper connector being configured to enable selective incremental adjustment of the upper cuff relative to the upper frame member for varying the arcuate dimension;

an upper cord selectively deployable between a connected configuration, wherein the upper cord is connected to the upper frame member and the upper cuff, and a disconnected configuration, wherein the upper cord is disconnected from one of the upper frame member and the upper cuff; and an upper mechanical tensioner rotationally coupled to one of the upper frame member and upper cuff and in operative communication with the upper cord, the upper mechanical tensioner being configured to incrementally increase the tension in the upper cord via rotation of the upper mechanical tensioner to urge the upper cuff toward the upper frame member;

wherein the gross adjustment upper connector includes a toothed band coupled to one of the upper frame member and the upper cuff member and a locking mechanism coupled to the other one of the upper frame member and the upper cuff member, the locking mechanism being moveable between an unlocked configuration and a locked configuration relative to the toothed band, the toothed band being moveable relative to the locking mechanism when the locking mechanism is in the unlocked configuration to adjust the distance between the upper frame member and the upper cuff member, the locking mechanism being engaged with the toothed band when the locking mechanism is in the locked configuration to mitigate movement of the toothed band relative to the locking mechanism.

2. A knee brace comprising:

a first assembly defining a first adjustment section and a first connecting section, the first assembly including a first frame member and a first cuff member;

a first gross adjuster coupled to the first frame member and the first cuff member, the first frame member and first cuff member being selectively connectable to each other via the first adjuster, the first adjuster being configured to enable selective incremental adjustment of the distance between the first frame member and the first cuff member adjacent the first adjustment section when the first frame member and first cuff member are connected to each other via the first adjuster;

a first connector coupled to the first frame member and the first cuff member and including a cord that is selectively extendable between the first frame member and first cuff member, the first connector being configured to enable selective engagement between the first frame member and the first cuff member adjacent the first connecting section;

a first mechanical tensioner coupled to the first assembly and in operative communication with the first connector and configured to increase the tension in the first connector in response to movement of the first mechanical tensioner relative to the first assembly; and a second assembly pivotally coupled to the first assembly;

wherein the first gross adjuster includes a toothed band coupled to one of the first frame member and the first cuff member and a locking mechanism coupled to the other one of the first frame member and the first cuff member, the locking mechanism being moveable between an unlocked configuration and a locked configuration relative to the toothed band, the toothed band being moveable relative to the locking mechanism when the locking mechanism is in the unlocked configuration to adjust the distance between the upper frame member and the upper cuff member, the locking mechanism being engaged with the toothed band when the locking mechanism is in the locked configuration to mitigate movement of the toothed band relative to the locking mechanism.

\* \* \* \* \*